United States Patent [19]

Packer et al.

[11] 4,048,325
[45] Sept. 13, 1977

[54] LOW TOXICITY METHOD OF INHIBITING SICKLING OF SICKLE ERYTHROCYTES

[75] Inventors: Lester Packer, Orinda; Edwin N. Bymun, Oakland, both of Calif.

[73] Assignee: The United States of America as represented by the United States Energy Research and Development Administration, Washington, D.C.

[21] Appl. No.: 646,707

[22] Filed: Jan. 5, 1976

[51] Int. Cl.$^2$ .................... A01N 1/02; A61K 31/21; G01N 1/30
[52] U.S. Cl. ........................................ 424/298; 424/3; 424/322
[58] Field of Search .................. 424/3, 298, 326, 327, 424/322; 260/453 RW

[56] References Cited

PUBLICATIONS

Raper, Ann, Soc. belge medtrop., vol. 49, 1969, pp. 205-210.
Lubin, Proc. Nat. Acad. Sci., USA, 72(1), pp. 43-46, Jan., 1975.
Dutton, Biochem. & Biophys. Res. Comm., vol. 23, No. 5, 1966, pp. 730-739.
Hunter, JACS, vol. 84, 1962, pp. 3491-3504.
Wheeler, Biochem & Biophys. Res. Commun., vol. 54, 1973, pp. 1024-1029.

Primary Examiner—Albert T. Meyers
Assistant Examiner—A. P. Fagelson
Attorney, Agent, or Firm—Dean E. Carlson; R. S. Gaither; Irene S. Croft

[57] ABSTRACT

A low toxicity method of inhibiting sickling of sickle erythrocytes which comprises intermixing the erythrocytes with an effective anti-sickling amount of a water-soluble imidoester of the formula $RC(=NH)OR'$ wherein R is an alkyl group of 1 - 8 carbon atoms, particularly 1 - 4 carbon atoms, and R' is an alkyl group of 1 - 4 carbon atoms, specifically methyl or ethyl acetimidate.

9 Claims, 2 Drawing Figures

LOW TOXICITY METHOD OF INHIBITING SICKLING OF SICKLE ERYTHROCYTES

BACKGROUND OF THE INVENTION

The invention described herein was made in the course of, or under, United States Energy Research and Development Administration Contract No. W-7405-ENG-48 with University of California.

This invention relates to a method of inhibiting sickling of human sickle erythrocytes, particularly for the treatment of sickle cell disease.

Persons who carry the sickle cell trait have an inherited abnormality of the hemoglobin caused by the mutation of the gene that determines the structure of one pair of the polypeptide chains of the hemoglobin. Sickle hemoglobin (hemoglobin S or HbS) differs from normal hemoglobin in that a single amino acid in one pair of the polypeptide chains has been replaced — glutamic acid by valine. Sickle cell anemia names the condition for persons having two genes for the abnormal hemoglobin. In this condition, most of the red cells of a sample of fresh blood look discoidal (the normal shape) until deprived of oxygen when the characteristic sickle-shaped forms with threadlike extremities appear. Re-exposure to oxygen causes immediate reversion. Sickle hemoglobin deprives the red blood cells of the ability to transport oxygen; persons afflicted with sickle cell anemia suffer constant sickling with resulting hemolytic anemia. Complications are multiple and severe, e.g. retarded growth, perodic attacks of pain from blood stasis, bone changes, neurological problems, and progressive kidney dysfunction, and increase with age. The complications are due to blockage of the capillary beds in various organs by masses of sickled red cells. Death from anemia, from infections, or, ultimately, from heart or kidney failure often occurs before the age of 35 – 40 years. In persons having only one gene for the sickle hemoglobin, the proportion of normal erythrocytes (red blood cells) is high enough to avoid anemia.

Up to now, treatment of sickle cell anemia has been limited mostly to relieving the symptoms. Recently, a number of compounds acting both covalently and non-covalently has been investigated to modify either the sickle erythrocyte or HbS in an effort to prevent sickling and aggregation of HbS. These modifications include treatment with aspirin, cyanate, anionic pyridoxal derivatives, procaine hydrochloride, organic solvents, protein denaturants such as urea and guanidine hydrochloride, and zinc. To represent a potentially useful antisickling agent, a compound must be effective in concentrations compatible with erythrocyte physiology. Furthermore, agents acting on HbS must be able to readily penetrate the erythrocyte membrane. Several of the aforementioned compounds must be employed at high concentrations. Moreover, although direct pyridoxylation increases the solubility of HbS, the alkylating agents employed have been shown to penetrate membranes poorly, resticting the interaction of these compounds with hemoglobin when added to cells.

More recently, dimethyl adipimidate (hereinafter referred to as DMA), a bifunctional crosslinking reagent that is known to link covalently the free amino groups in polypeptides, was reported to inhibit sickling in vitro (B, H, Lubin et al, "Dimethyl Adipimidate: A New Antisickling Agent," *Proc. Nat. Acad. Sci. USA* 72(1), pp. 43–46, January, 1975). Although bifunctional imidates such as DMA have been found to prevent sickling at very low concentrations, these reagents have also been found to be deleterious to several membrane systems; hence, the potential exists for adverse side effects when used as therapeutic agents for the treatment of sickle cell disease.

SUMMARY OF THE INVENTION

Broadly, the present invention provides a method for inhibiting anoxia-induced sickling of sickle erythrocytes with an effective antisickling amount of a water-soluble monofunctional imidoester having the general formula $RC(=NH)OR'$ where R is an alkyl group of 1 – 8 carbon atoms, preferably 1 – 4 carbon atoms, and $R'$ is an alkyl group of 1 – 4 carbon atoms, preferably a methyl or ethyl group. It has been found that at comparable levels of amidination, monimidates are signficantly less deleterious to the biological oxidation and bioenergetic activites of the energy transducing systems of mammalian mitochondria and plant chloroplasts that their bifunctional analogues.

It is, therefore, among the objects of this invention to provide a method for inhibiting sickling of sickle erythrocytes, particularly for the treatment of sickle cell disease.

It is a further object of this invention to provide a method for inhibiting human sickling which has minimal potential adverse side effects on metabolism.

Other objects and advantages will become apparent from the following detailed description made with reference to the accompanying drawings.

DETAILED DESCRIPTION OF THE INVENTION

Figure 1:
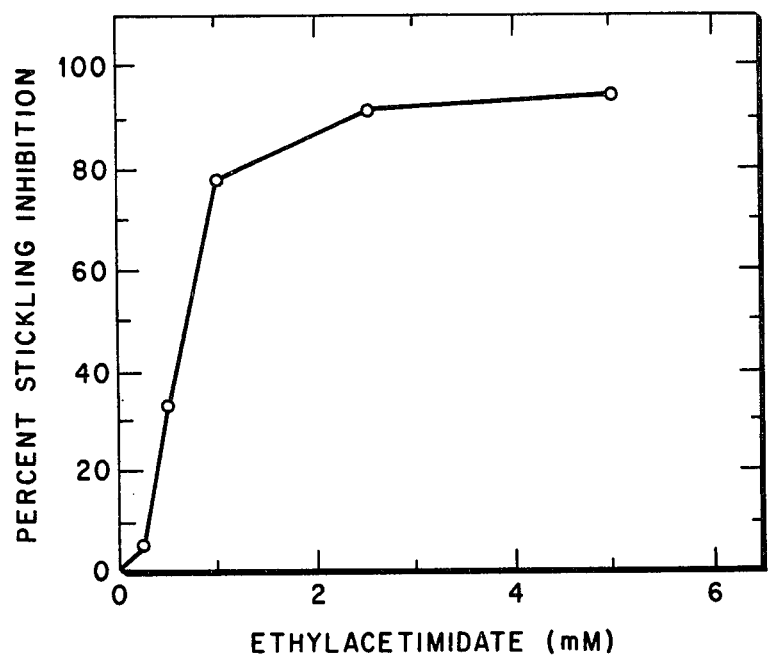
FIG. 1 is a graph illustrating the effect of ethyl acetimidate (EA) on in vitro sickling.

In accordance with the present invention it has been found that anoxia-induced sickling of sickle erythrocytes is inhibited by intermixing the erythrocytes with an effective anti-sickling amount of a water-soluble imidoester having the general formula $RC(=NH)OR'$ where R is an alkyl group of 1 – 8 carbon atoms, preferably 1 – 4 carbon atoms, and $R'$ is an alkyl group of 1 – 4 carbon atoms, preferably a methyl or ethyl group. The ethyl monoimidates are preferred since the ethyl group hydrolyzes to ethyl alcohol which is a metabolite. Specific reagents useful in the present invention are methyl acetimidate, ethyl acetimidate (hereinafter referred to as EA) and methyl butyrimidate. The resulting modified erythrocytes were found to display minimal alteration of both rheological and metabolic properties.

Treatment of human patients afflicted with sickle cell anemia can be accomplished either extracorporeally or intravenously by the method of the present invention. Extracorporeal treatment is effected by blood exchange, that is, blood is removed from the patient, treated with a monoimidate as specified above, and the treated blood is then returned to the patient. Alternatively, and preferably, treatment can be effected by injecting directly into the bloodstream of the patient a pharmaceutical composition comprising an effective antisickling but non-toxic amount of the above specified monoimidate and a suitable pharmaceutical carrier such as sterile water. A suitable buffering agent may be added to the injectable composition to maintain the pH levle thereof at substantially 7.4, the normal pH level of human blood.

The monofunctional imidoesters used in the present invention were found to be 70 - 80% effective in vitro at concentrations as low as 1 mM with nearly complete inhibition of sickling occuring at concentrations in the range of from about 2 to about 5 mM, as illustrated in the following example using ethylacetimidate.

EXAMPLE

Materials

Fresh heparinized sickle blood was obtained from Children's Hospital, Oakland, CA (Courtesy Dr. B. Lubin). Normal blood was obtained from healthy volunteers. Ethylacetimidate (EA) hydrochloride was provided by Peter Nemes, George Miljanich, and Dr. Edward Dratz, Department of Biochemistry, University of California, Santa Cruz. Krebs-Henseleit Buffer (280mOsM), referred to as KHB, is made up from a standard stock of reagents that contain: $CaCl_2$, 12g/l — 2.8 ml; KCl, 11.5g/l — 32 ml; NaCl, 60.63g/l — 50 ml; $KH_2PO_4$, 21.1g/l — 8 ml; $NaHCO_3$, 52g/l — 84 ml; $MgSo_4$, 38.2g/l — 8 ml; distilled $H_2O$ — 825.2 ml; total — 1000 ml.

Amidination

Cells were washed with Krebs-Henseleit Buffer (pH 7.4) to remove non-erythrocyte blood elements and resuspended in the same medium to a final hematocrit of 20-40%. Erythrocyte suspensions (4% hematocrit) were incubated in KHB (pH 8.5) containing freshly dissolved EA (1-10 mM). After incubation at room temperature (20°-22°) for 30 min, the cells were washed twice with KH buffer (pH 7.4) and resuspended either in the original plasma (40% hematocrit) for analysis of sickling or in other solutions as described below. To amidinate under anoxia the cells were equilibrated with nitrogen in a tonometer until no oxygen could be detected polarographically. Imidates were added in the dry state to anaerobic cell suspensions. Following treatment, the suspensions were diluted 1:1 with 0.1M Tris-acetate—0.15M NaCl buffer (pH 6.0) to quench amidination, and the cells washed as described above.

Sickling

Anoxic conditions

The cells were deoxygenated with freshly prepared sodium metabisulfite, fixed with 10% formaldehyde, and examined microscopically. Hypoxic conditions: Cell suspensions were deoxygenated by equilibration with 3% oxygen. Five hundred cells were conted to ascertain the extent of sickling.

Hemoglobin — Oxygen Affinity

The oxygen affinity of whole blood ($P_{50}$) was determined in a tonometer as in B. H. Lubin et al, cited above.

Preparation of ghost membranes

Erythrocytes were hemolyzed in 5mM sodium phosphate (pH 8.0) and membranes prepared as described by Fairbank et al, (1971) Biochemistry 10, 2606-2617.

Sodium Dodecylsulfate (SDS) — Polyacrylamide Gel Electrophoresis

Membranes and hemolystate (2-4 mg protein/ml) were solubilized in 1% SDS and 1% mercaptoethanol and electrophoresed in gels containing 6% acrylamide and 0.1% SDS as described by Melnick et al (1973) Biochem. Biophys. Acta 311, 230-241. Proteins were visualized after staining with Coomassie brillant blue as described by Fairbanks et al, op. cit.

Analytical Methods

Free amino groups were determined fluorometrically using fluorescamine (obtained from Hoffman-LaRoche, Nutley, New Jersey) as described by Bohlen et al (1973) Arch. Biochem. Biophys. 155, 213-220. Proteins was determined by the method of Lowry et al (1951) J.Biol. Chem. 193, 265-275.

The effect of EA on in vitro sickling is shown in FIG. 1. Under the above-described experimental conditions, erythrocytes incubated with 1 mM EA displayed approximately 70-80% prevention of sickling with nearly complete inhibition occurring with 2-5 mM EA. Negligible hemolysis was detected following the incubation under the conditions of amidination. EA was found to be effective under both hypoxic and anoxic conditions, indicating that factors other than altered oxygen affinity are involved.

In order to ascertain the extent of reaction of the imidates with cell components, amidinated erythrocytes were fractionated into membrane preparations and hemolysates. Flurometric analysis of primary amines indicated that treatment with EA resulted in amidination of both erythrocyte membrane and hemoglobin. The extent of reaction was minimal as less than 6% of the free amines were amidinated in both preparations after treatment with 2mM EA.

SDS-polyacrylamide gel electrophoresis was used to examine the polypeptide profile of membrane and hemolysate fractions isolated from amidinated sickle erythrocytes. Membranes isolated from amidinated sickle cells were similar to those of untreated controls. The similarity between control and amidinated material indicates that treatment does not cause the elution of membrane material. At higher concentrations of EA (> 5mM), extensive polymerization of both globin and membrane polypeptide occurred. The results suggest that low imidate concentrations (1-2mM) cause little alteration of erythrocyte polypeptides, even through these concentrations are effective in inhibiting sickling (approximately 80% inhibition).

Since oxyhemoglobin and deoxyhemoglobin differ in quaternary structure and since the structural differences may affect the manner in which imidates react with hemoglobin, amidination was carried out in the presence and absence of oxygen and the effect on oxygen affinity was then examined. The results are given in Table I.

TABLE I

THE EFFECT OF AMIDINATION ON HEMOGLOBIN-OXYGEN AFFINITY

| SAMPLE | IMIDATE CONCENTRATION | $P_{50}$ (mm Hg) oxy-genated | deoxy-genated |
|---|---|---|---|
| NORMAL CELLS | 0 | 27.0 | |
| SICKLE CELLS | 0 | 31.0 | |
| NORMAL CELLS | EA (1 mM) | 25.0 | 28.0 |
| SICKLE CELLS | EA (1 mM) | 27.0 | 35.0 |

Treatment of normal cells with low concentrations of EA under oxygenated conditions resulted in a slight increase in oxygen affinity. A greater increase in oxygen affinity was obtained when sickle cells were treated under identical conditions. The $P_{50}$ values displayed by modified sickle cells approximated those of untreated or treated normal cells (25-27 mm Hg). Conversely, normal and sickle cells treated under anoxia exhibited an increase in $P_{50}$ values (indicating a decrease in oxygen affinity) with the latter preparation showing the greatest increase. Sickle cells were in the sickle configuration during treatment under anoxia. An examination of the cells following amidination revealed that they were still sickled. However, cells resumed a discoid shape when reoxygenated. When the cells treated under anoxia were once again deoxygenated, sickling was prevented to the same degree as was obtained when amidination was carried out initially in the presence of oxygen.

Although the exact mechanism by which monoimidates inhibit sickling is not known, and direct evidence concerning the physical state of amidinated hemoglobin is unavailable, the foregoing experiments indicate that the antisickling mechanism is independent of effects on oxygen affinity and suggest a direct effect of the imidates on hemoglobin. The results suggest that substitution of amidino for amino groups prevents the aggregation of deoxyhemoglobin S. Furthermore, the low levels of monoimidates required to prevent sickling suggest that the number of amino groups may be small. The amino groups involved also appear to be as readily available in gelled hemoglobin S as in ungelled hemoglobin.

Two other monoimidates, methylbutyrimidate and methylacetimidate, were tested and found to be as effective as EA in preventing in vitro sickling. Furthermore, treatment with methylacetimidate resulted in the elimination of the net potassium leak which accompanies sickling.

When compared to bifunctional imidates, monoimidates have major advantages as therapeutic agents for the treatment of sickle cell disease. One important difference between the two classes of reagents is their relative effect on enzyme activity. It has been found that at comparable levels of amidination, monoimidates are significantly less inhibitory of electron transport and ATPase activities of mitochondrial inner membranes than their bifunctional analogues. Specifically, membranes treated with EA and dimethylsuberimidate (hereinafter referred to as DMS), a biimidate similar to DMA but possessing a longer chain, were compared with respect to electron transport and ATPase activities. The results as shown, respectively in Table II and FIG. 2. To facilitate a comparison of imidate action, effects were related to extent of amidination as measured by percent amino group decrease rather than the absolute reagent concentration.

TABLE II

| | THE EFFECT OF AMIDINATION ON ELECTRON TRANSPORT | | | |
|---|---|---|---|---|
| | | Activity (% control) | | |
| | %NH$_2$ loss | NADH oxidase | Succinate oxidase | Ascorbate-TMPD oxidase |
| Control | | 100 | 100 | 100 |
| 2 mM DMS | 16 | 58 | 62 | 61 |
| 10 mM DMS | 41 | 10 | 22 | 28 |
| 4 mM EA | 16 | 78 | 61 | 73 |
| 20 mM EA | 46 | 56 | 45 | 64 |

As shown in Table II, nicotinamide adenine dinucleotide (NADAH) oxidase, succinate oxidase, and ascorbate - N, N, N', N'-tetramethyl -p- phenylenediamine (TMPD) oxidase were markedly inhibited by DMS treatment. At comparable levels of amidination all activites were significantly less sensitive to EA than DMS treatment.

Figure 2:
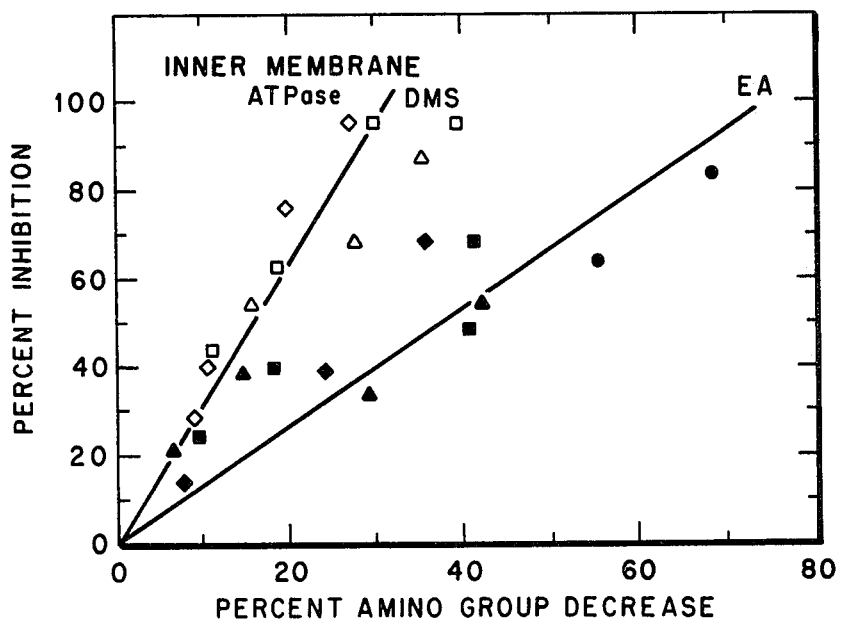
FIG. 2 is a graph illustating the effect of dimethylsuberimidate (DMS) and ethylacetimidate (EA) on inner membrane ATPase (adenosine triphosphatase) activity. Open symbols represent DMS-treated membranes, and closed symbols represent EA-treated membranes.

ATPase activity ($\mu$mole hydrolyzed/min/mg preotein) was also markedly inhibited by treatment with DMS (FIG. 2). At comparable levels of amidinations, the monofunctional reagent Ea was significantly less inhibitory than the bifunctional imidate DMS. In the experiment designated by the closed circles in FIG. 2, membranes were treated with high concentrations of EA to determine the extent of amidination required for complete inhibition of activity. The concentrations of EA required for complete inhibition of activity are considerably in excess of the amount required to inhibit sickling.

Additionally, monofunctional imidates do not affect the osmotic fragility of human erythrocytes whereas the bifunctional imidates, particularly at higher concentrations, do so. Since an essential prerequisite for a functioning erythrocyte is the ability of the cell to deform in order to pass through small capillaries, it is evident that monoimidates are much more suitable as therapeutic agents than the bifunctional analogues.

In experiments conducted to determine the effect of monoimidates on animal survival, rats were treated with ethylacetimidate at levels of 30mM in whole blood under conditions similar to the in vitro studies described above. This level fo treatment is at least 30 times higher than required for prevention of sickling in vitro. At least three-fourths of the blood was treated and exchanged. In three individual experiments no deleterious effects were found although the hematocrits were slightly reduced after such treatment in the animals due to the loss of blood during the transfusion.

Toxicity tests on DMA and EA were carried out by intraperitoneal injections in both mice and rats. Each compound was made up in KH buffer (280 Mosm) buffered to pH 7.4 with 5N NaOH. The final volume for each injection was 1 cc in rats in 0.5 cc in mice. The results were as follows:

Mice LD$_{50}$ (Lethal dose for 50% of the animals)
DMA 750 mg/kg body wt
EA 950 mg/kg body wt
Rats LD$_{50}$
DMA 700 mg/kg body wt
EA 900 mg/kg body wt The results clearly show that monofunctional imidates such as EA are less toxic in animals than bifunctional reagents.

As stated above, the preferred method of treating human patients suffering from sickle cell disease is by injecting a pharmaceutical composition comprising a monoimidate as specified herein directly into the bloodstream. Since the present method of treatment is effective either in the absence or the presence of oxygen, injection may be either into a vein or an artery, preferably a vein A pharmaceutically acceptable non-toxic inert diluent such as sterile water can be used as a carrier. The amount of monoimidate present in the composition should be such as to provide a concentration level in whole blood effective for the prevention of sickling of the erythrocytes but below the toxicity level of the reagent. A level in whole blood of the order of magnitude of from about 1 to about 10mM of monoimidate, preferably in the range of from about 2 to about 5mM, is suitable. A buffering agent such as KHB, PH 7.4, or any buffered saline solution which does not contain a reactive amino group, may be added to the composition to maintain the pH level at substantially 7.4.

Although the invention has been described with respect to specific examples, it is to be understood that various other embodiments and modifications will be obvious to those skilled in the art, and it is not intended to limit the invention except by the terms of the following claims.

What we claim is:

1. A method of inhibiting sickling of human sickle erythrocytes which comprises intermixing the erythrocytes with a water-soluble monofunctional imidoester having the general formula $RC(=NH)OR'$ wherein R is an alkyl group of 1–8 carbon atoms and R' is an alkyl group of 1–4 carbon atoms in a amount effective to inhibit sickling and below the toxicity level of the imidoester.

2. A method according to claim 1 wherein the intermixing of the erthrocytes and the mono-functional imidoester is accomplished extracorporeally.

3. A method according to claim 1 wherein R is an alkyl group of 1–4 carbon atoms.

4. A method according to claim 3 wherein R' is a methyl or ethyl group.

5. A method according to claim 4 wherein the imidoester is ethylacetimidate.

6. A method according to claim 4 wherein the imidoester is methylacetimidate.

7. A method according to claim 4 wherein the imidoester is methylbutyrimidate.

8. A method according to claim 1 wherein the amount of imidoester is equivalent to a concentration of imidoester in whole blood in the range of from about 1 mM to about 10 mM.

9. A method according to claim 8 wherein the amount of imidoester is equivalent to a concentration in whole blood in the range of from about 2 mM to about 5 mM.

* * * * *